United States Patent
Peng et al.

(10) Patent No.: US 6,997,347 B2
(45) Date of Patent: Feb. 14, 2006

(54) APPARATUS AND METHOD FOR GENERATING CALIBRATION GAS

(75) Inventors: Wenfeng Peng, Oakdale, PA (US); David C. Green, Canonsburg, PA (US); Robert G. Stewart, McDonald, PA (US)

(73) Assignee: Industrial Scientific Corporation, Oakdale, PA (US)

( * ) Notice: Subject to any disclaimer, the term of this patent is extended or adjusted under 35 U.S.C. 154(b) by 348 days.

(21) Appl. No.: 10/610,632

(22) Filed: Jul. 2, 2003

(65) Prior Publication Data

US 2005/0000981 A1    Jan. 6, 2005

(51) Int. Cl.
  *G01N 31/00*    (2006.01)

(52) U.S. Cl. ............... 222/3; 222/5; 222/1; 222/145.6; 73/1.04

(58) Field of Classification Search ............... 222/1, 222/3, 5, 145.6; 73/1.04
See application file for complete search history.

(56) References Cited

U.S. PATENT DOCUMENTS

| | | | | |
|---|---|---|---|---|
| 4,531,398 A | * | 7/1985 | Di Benedetto et al. | 73/1.04 |
| 5,214,952 A | * | 6/1993 | Leggett et al. | 73/1.03 |
| 6,234,001 B1 | * | 5/2001 | Sorensen et al. | 73/1.04 |
| 2004/0216508 A1 | * | 11/2004 | Hirsch et al. | 73/1.04 |

* cited by examiner

*Primary Examiner*—J. Casimer Jacyna
(74) *Attorney, Agent, or Firm*—Dennison, Schultz, Dougherty & MacDonald

(57) ABSTRACT

An apparatus and method for generating a low concentration of gas within a carrier gas flow employing one or more miniature one-piece cylinders filled under pressure with a pure gas, or a concentrated gas balanced with an inert gas or gas mixture. Released from the cylinder through a pierced or other controlled opening, the flow of the gas is regulated by a pressure regulator and a micro orifice to be blended into a steady stream of diluent gas, typically ambient air, to form a desired gas concentration. No gas is generated if the pressure of the gas in the cylinder, which is monitored constantly by a pressure transducer, is below a predetermined level. The apparatus can be built into a portable device, or an automated docking station (or calibration station) for testing and calibrating gas detection and monitoring instruments, or into a fixed gas detection system for performing such functions.

24 Claims, 3 Drawing Sheets

APPARATUS AND METHOD FOR GENERATING CALIBRATION GAS

BACKGROUND OF THE INVENTION

1. Field of the Invention

The invention relates to an apparatus and method employing one or more miniature one-piece gas cylinders, for producing low concentration gases for testing and/or calibrating gas monitoring instruments.

2. Description of Related Art

Gas detection instruments are widely used to safeguard human lives and property in various industries in, for example, potentially explosive environments such as mines having methane ($CH_4$) pockets, confined spaces where there exist toxic gases such as carbon monoxide (CO) and hydrogen sulfide ($H_2S$), or a deficiency of oxygen, and chemical process plants where emissions may include sulfur oxide ($SO_x$), nitrogen oxide ($NO_x$), chlorine ($Cl_2$), etc. The heart of each instrument is comprised of sensors that convert chemical energy to electrical energy. The most common sensors include metal oxide semiconductor (MOS) sensors, thermal conductivity sensors, catalytic bead sensors, electrochemical sensors, infrared sensors, and photo ionization detectors. Some types of sensors react with the gas and cause a permanent change in gas molecules and are destructive to the gas sample. Other sensors do not cause a permanent change in gas molecules and are nondestructive technologies. Gas reactions and environmental factors can change sensor performance as well; all sensors are subject to changes in gas sensitivities and sometimes in response times as well. Typically a sensor will gradually lose sensitivity due to environmental or aging effects. In some severe weather conditions, a sensor can lose sensitivity within a very short period of time. For example, a galvanic type oxygen sensor can fail suddenly when the capillary hole, through which oxygen diffuses into the sensor cell, is blocked by water or dust. Some electrochemical sensor can fail rapidly due to leakage of electrolyte. Catalytic bead sensors that are used for detecting combustible gases, can lose sensitivity without any indication after exposure to silicone compounds which poison sensors by building up a solid coating over catalyst sites which blocks gas reactions. The use of a defective, low sensitivity instrument is extremely dangerous as it often gives a false, misleading reading, putting human lives and property in great danger.

In order to maintain gas detection instruments in a working condition, regular calibrations are required. A gas of known concentration, often called a calibration gas (cal gas), must be used as a reference gas. During calibration the instrument is first exposed to clean air free of pollutant, and is then exposed to the calibration gas until a steady state reading is established. The span reading is then compared to the nominal value of gas concentration, and if the reading is the same as the gas concentration then the instrument is considered accurate; otherwise the instrument needs to be corrected. Instrument readout is typically corrected through adjusting a potentiometer in the hardware, or applying a correction factor to raw data in the software. Normally calibrations are performed by trained personnel on a monthly basis. In applications where heavy usage or harsh environments are involved, instruments are required to be calibrated on a more frequent basis, e.g. once a week.

Regular calibrations ensure accuracy of the instrument immediately after calibration. Sensors can, however, fail between calibrations, and instrument users are advised to verify their instrument functionality prior to each use. Such a test is generally referred to as a bump test, in which the instrument is exposed briefly to the gas it's intended to detect to cause a response from the sensor. If the instrument reading is prompt and is within a pre-determined percentage window with reference to the test gas concentration, the instrument is considered to be working properly.

At the present time, most instrument calibrations and tests are done with pressurized, premixed gases, which are supplied from steel or aluminum cylinders. Each cylinder has a valve on the top of the cylinder; upon connecting to a pressure or flow regulator the normally closed valve is open, and when the valve within the attached regulator is opened, the gas is released from the cylinder. Any instrument connected to the system is subsequently exposed to the gas.

Premixed calibration gases are simple to use. Because a gas can be certified before filling a cylinder, no gas mixing is involved thereafter and the use of a pre-mixed calibration gas offers accuracy in gas concentration. If the gas is unstable or reactive, however, it will have a short life and poor accuracy especially when the concentration is in the low parts per million (ppm) range. Such gases include ozone ($O_3$), nitrogen dioxide ($NO_2$), chlorine dioxide ($ClO_2$), chlorine, hydrogen sulfide, etc. Moreover, pre-mixed gases are very expensive. A typical disposable cylinder having 58 liters of gas generally costs between $100–350. Such cylinders are also large in size and are inconvenient to transport and carry in the field.

Typically, a single calibration event consumes between 1–4 liters of calibration gas, so the most popular disposable gas cylinders having 34 or 58 liters of gas would last for only about 10–50 calibrations, at a cost of over $2 for each calibration. In order to cut down the cost, calibration gases are often obtained by diluting gas with mass flow controllers (MFCs) in the laboratory. A MFC controls the rate of gas flow with two pressure transducers placed downstream and upstream, respectively. Two large size cylinders, one of which being a diluting gas, are employed. When the gas of interest and the diluting gas are controlled by two MFCs at preset flow rates, the output gas mixture has a concentration determined by the ratio of the two gas flow rates.

In spite of simple operation and calculation, normal MFCs can't be used for diluting gas accurately at a dilution ratio greater than 10:1. Therefore, the concentration of the source gas must not exceed 10 times that of the desired calibration gas. For example, nitrogen dioxide ($NO_2$) sensors are typically calibrated at 10 ppm by volume. The maximum concentration of $NO_2$ as a source gas for dilution should be 100 ppm, or 0.01% by volume. This means a gas has to be diluted to a very low concentration, either by the gas supplier or by the user, prior to diluting with MFCs in the lab to produce a ppm—level concentration suitable for calibration use. Successive dilutions significantly increase error in the final gas concentration, not to mention the inaccurate concentration of the source gas. According to gas manufacturers, the lower the concentration of a gas in a gas mixture, the higher the error in gas concentration. A gas can be prepared with a tolerance well within ±1–2% when its concentration is above 1% by volume, but it's difficult to make it better than ±5% when its concentration is below 1000 ppm. Besides, mass flow controllers are very expensive, gas generators built with mass flow controllers are usually cost prohibitive.

A pure or concentrated gas makes a much larger quantity of calibration gas than an equal amount of low concentration gas. By using a highly concentrated gas, the volume of the source gas under the same pressure, and thus the size of the cylinder storing the gas and the generator employing the cylinder, can be substantially decreased.

Pure gases in small containers have been employed for calibrating and testing laboratory gas analyzers. They are called permeation devices or permeation tubes. A permeation tube is a small, inert tube containing a pure chemical compound in a two-phase equilibrium between its gas phase and its liquid (or solid) phase. At a constant temperature, the tube emits the compound through its permeable wall at a constant rate, which is then mixed with a carrier gas at a controlled flow rate to obtain a known mixture. Permeation tubes must be used with precise temperature control ovens or apparatus, which are bulky and expensive. They can't be turned off once activated. Although a wide range of permeation rates can be made by varying the length and thickness of the tubes, the normal operating rates range from 5 ng/min to 5 $\mu$g/min, or in the parts per billion (ppb) range when diluted to 500 ml/min which is a flow rate typically required for calibrating gas detection instruments in the safety market; they are not, therefore, suitable for gas monitoring applications.

Attempts have been made to generate gases at constant rates immediately before use through photo-chemical, electrochemical, thermo-chemical and other chemical processes. For example, U.S. Pat. No. 3,752,748 discloses an ozone generator, which utilizes a photochemical method. Electrochemical gas generators for generating $H_2S$, $H_2$, $Cl_2$ and some other gases are described in U.S. Pat. No. 5,395,501. The generators comprise an electrochemical cell having gas generating and counter electrodes with an intervening body of electrolyte; electric current passing between the electrodes causes the generation of gas at the gas-generating electrode. In this electrochemical type generator, the gas is generated when needed and the rate of its production, and thus also its concentration in a carrier gas, is controlled through the current that passes through the electrolytic cell.

In addition to the chemical gas generating methods, a gas of low concentration can also be generated from its liquid phase if the boiling point of the species is higher than ambient temperature. For example, U.S. Pat. No. 6,234,001 discloses an apparatus for generating calibration gas comprising a contained stream of carrier gas, and a chamber containing at least part of the stream and a volatile reference liquid are held by a wick structure so that as the stream passes through the chamber, the volatile reference liquid evaporates into a gas that blends into the carrier gas to form a calibration gas.

On-site gas generation methods and apparatus as described are available for a very limited number of gases. They suffer from poor accuracy, too. The most used test gases such as carbon monoxide and methane cannot be produced in a reliable, controlled manner through chemical or evaporation processes.

SUMMARY OF THE INVENTION

It is therefore a primary object of the invention to provide an apparatus and method for generating a calibration standard gas at low cost using a device that is portable, compact, and capable of generating gas on demand with accurate gas concentrations.

To achieve these and other objects, the invention is directed to an apparatus for providing calibration gas to a gas monitoring instrument, comprising:

a calibration gas source comprising a miniature gas cylinder containing a calibration gas, and including a pierceable seal or open/close valve;

an outlet for providing test gas to the monitoring instrument; and a gas conduit for providing diluted cylinder gas to the outlet, the gas conduit comprising:

a receptacle means for receiving the miniature gas cylinder in gas-tight manner, and including means for rupturing the seal or opening the valve;

a manifold;

pressure transducer means for determining pressure of the gas in the conduit;

a valve for releasing the gas into the gas conduit;

a micro orifice for providing a controlled flow of calibration gas in the conduit;

means for diluting gas in the conduit with air; and control means for releasing test gas to the conduit upon determination of sufficient pressure in the manifold.

The invention is further directed to a method for providing a calibration gas to a gas detection instrument, comprising the steps of:

disposing in a receptacle a miniature gas cylinder containing a calibration gas, and opening a seal in the cylinder to permit gas to flow into a gas conduit;

determining pressure of the gas in the conduit, and verifying that said pressure is at least a predetermined level;

passing the gas which is at least at said predetermined pressure through a micro orifice to control the flow of the gas to a predetermined rate;

diluting the gas flowing at said predetermined rate with a diluting gas flowing at a known rate; and passing the diluted gas to an instrument to be calibrated.

Miniature cylinders filled with a concentrated gas provide an excellent solution to gas generation. Miniature gas cylinders having a capacity of less than 100 ml filled with liquid or a compressed gas are generally referred to as gas cartridges. They are deep drawn, one piece steel or aluminum filled under pressure with a specified gas to a specified quantity and then sealed-for-life with a pierceable cap enclosure. The cap is usually welded or crimped. Because such cylinders do not leak, they are not considered dangerous goods and are exempt from government high pressure gas transportation regulations. In the United States, gas cartridges may be shipped by ground transportation as a Consumer Commodity.

Portable pressurized gases are a remarkably versatile working fluid. They have been used widely in military, medical, and sports and safety markets such as life jackets and tire inflators, oxygen inhalers, sporting guns, fire extinguishers, mini flame torches, soda siphons and cream whippers, etc. Presently, a complete range of cylinders containing air, carbon dioxide ($CO_2$,), oxygen ($O_2$), nitrogen ($N_2$), helium (He), nitrous oxide ($N_2O$), propane, sulfur hexafluoride ($SF_6$) and gas mixtures are commercially available, with some of them being priced under \$1 each.

Such a miniature gas cylinder can make a large quantity of gas. For example, a miniature cylinder having a 10 ml water capacity holds 340 ml CO gas when the gas pressure is 500 psi, which is about 60 times the quantity of CO in a standard disposable cylinder filled with 58 liters (2 $ft^3$) of 100 ppm gas under the same pressure. Because of the very limited quantity of the gas contained in the miniature cylinder, it will not endanger human life if it accidentally leaks out. In a confined space as small as 10 $m^3$, the highest concentration caused by a leaking cylinder is 34 ppm by volume, which is low and safe. A 10 ml cylinder filled with pure methane under 2000 psi holds a quantity of gas that is equivalent to 1360.5 ml at 1 atmosphere. When diluted to the same confined space, the gas concentration will be 136 ppm by volume, which is far below its lower explosion limit of 5%, or 50,000 ppm by volume.

Gas generators built with miniature gas cylinders can be very compact. They can be designed as portable instruments for use with portable gas detection instruments. They can also be incorporated into fixed gas detection systems for conducting regular bump testing and automatic calibration. Regular testing and calibration gases have been a large expense to instrument owners and especially to the owners of fixed systems as a field trip is often involved. Considering the large quantity of calibration gas that a miniature cylinder can supply, a gas generator made according to the invention can work as an automated, stand alone test station. The generator can have multiple cylinders, with each cylinder being a one piece miniature cylinder filled with concentrated gas for generating low concentration gases used to test and/or calibrate multiple instruments. There is a trend in the gas detection industry of making computerized calibration/test stations; a number of instruments, including single gas detectors and multiple gas detectors, can be docked on the station. The computer recognizes each instrument and only gases of interest are introduced to the instrument. Docking stations conduct gas testing and calibration on a more frequent basis, thus gas usage has greatly increased. Gas generators built according to the invention meet this challenge, and can be installed in small offices without safety concerns.

The concentration of gas in the cylinder will normally be at least 0.1% by volume, preferably 1–100% by volume, and is often "pure", with "pure" being defined as a gas concentration at least 98% by volume. The gas in the cylinder is balanced by a gas or gas mixture with which it does not react. For example, $H_2S$ is oxidized slowly by oxygen, so it would not be blended with air for long term storage, but $H_2S$ can be blended with nitrogen, with which it does not react. CO is a non-reactive gas, and can be diluted with air for storage.

Unlike conventional calibration methods in which dry air is used as the balancing gas and is mixed with the gas of interest or stored in a separate cylinder, a preferred embodiment of the invention utilizes ambient air as the diluting gas, and preferably ambient air which has passed through a chemical filter. The air is delivered at a constant flow rate through an appropriate means, so that when mixing with a constant flow rate of gas from a cylinder, a stream of gas is formed with a desired concentration of the gas of interest. Because of the ready availability of ambient air, only the miniature gas cylinder needs to be mounted in the generator. By diluting a pure or concentrated gas from the cylinder, a more accurate gas concentration can be obtained than in situations where an already diluted low-concentration gas is again diluted.

DESCRIPTION OF THE PREFERRED EMBODIMENTS

Figure 1:
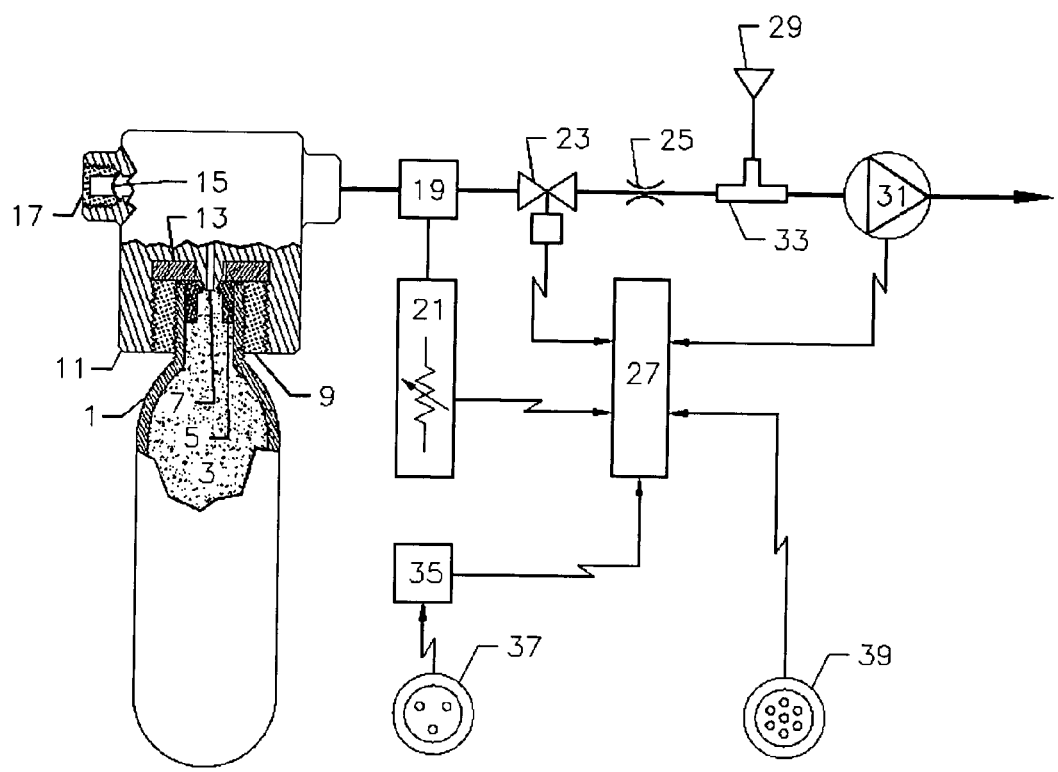
FIG. 1 is a schematic representation of a gas generator according to a first embodiment of the present invention.

FIG. 1 illustrates a gas generator built with a miniature gas cylinder, or cartridge. The generator includes a gas source, a gas dilution device, and a control system. The techniques used to provide diluted, low concentration gas are basically pneumatic pressure regulation and flow control.

The source of gas includes a miniature gas cylinder, a gas release device and a flow control system. As shown, the gas source is a miniature gas cylinder 1 of no more than 100 ml internal volume containing a compressed, concentrated gas 3, and closed by a welded cylinder cap 5. The cylinder cap 5 is specially constructed with a reduced thickness portion in the center of the cap, which facilitates piercing of the cylinder during installation. Cylinder 1 is held by a threaded neck and seal retainer 9 in a gas cylinder receptacle 11 which includes a piercing device 7 that punctures the reduced thickness portion of cap 5 to release the contents of the cylinder into the receptacle 11. The piercing device can be embodied in a number of different shapes all of which will produce the same effect; preferably, the piercing device will remain fixed. Alternately, however there can be a knob or automated mechanism in place of the fixed receptacle. In this case, the pin would be lifted or moved prior to installing the compressed gas cylinder.

In lieu of piercing, the compressed cylinder may also be constructed with a valve that can be either manually or electrically actuated to empty the cylinder's contents into the receptacle. In this embodiment, the valve takes the place of the reduced thickness portion of the cylinder cap 5. Valve types include direct release, shut-off valve, fixed pressure and direct release, and constant flow valve, etc. If properly constructed, it would also be possible to use the piercing pin 7 of the receptacle 11 to open the cylinder valve and thereby allow one type of cylinder receptacle/regulator to satisfy both types of cylinders.

Receptacle 11 may optionally include a pressure regulator built therein. The pressure regulator regulates the output pressure of the gas to a constant, low pressure. The receptacle 11 is equipped with an over-pressure safety vent 17 that retains a rupture disk 15. When the pressure in the receptacle is above a predetermined level and determined to be unsafe, for example 5000 psi, due to heat or installation of an over-pressurized cylinder, etc., the rupture disk will burst and allow pressurized gas to vent from the system.

Once the cap 5 is pierced or the cylinder valve is opened, the gas inside the cylinder 1 will fill the internal volume of the gas cylinder receptacle 11. Due to the small volume of the compressed gas cylinder, it is necessary to minimize the overall volume of the gas receptacle 11 and the remaining volume of the device. This will minimize over-dilution of the gas of interest in the final delivered product. In order to prevent gas from leaking out when installing the cylinder, a rubber gasket 13 is disposed in the recess of the receptacle 11. The thickness and material of the gasket 13 has been selected so that a sufficient seal is created prior to piercing of the cylinder cap 5.

A manifold 19 is provided either as part of or separate from the receptacle 11, as the outlet for the gas in the cylinder, passing the gas downstream through a solenoid valve 23 and a precision micro orifice 25. A pump 31 connected to the micro orifice 25 passes the gas in the direction of the arrow to a gas detection apparatus to be tested (not shown). In order to dilute the test gas, a mixing tee 33 is disposed between the micro orifice 25 and the pump 31, with air being admitted to the tee 33 through an air filter 29.

Gas pressure in the manifold 19 is measured by pressure transducer 21, and the entire system is under the control of a control means 27, typically a circuit board with a microcontroller and the necessary support circuitry. A power supply 35 is provided to power the system, and the power can be supplied by the line power or batteries via a connector 37. The microprocessor/microcontroller receives signals from the pressure transducer or switch 21, and controls the solenoid valve 23 and the air pump 31. Upon demand, the controller implements all of the previously described functions to enable and disable the gas generation process. An external data connection 39 may be provided for status reporting and controlling or scheduling of use of the system by external means. As an alternative, the controller may include wireless communication means built therein.

After installation of the cylinder, the knob or lever connected to the piercing device 7 may be manually operated, or may be moved by a mechanism operated by control system 27. It is however a requirement that any type of piercing pin operate in such a manner as to prevent significant cylinder leakage.

A typical single stage regulator, such as a regulator built into receptacle 11, has an output variation of about 10% which represents the maximum pressure difference at the outlet of the regulator between a new, full cylinder and one that is spent. Because the output pressure of the regulator is equal to the inlet pressure of the gas at the micro orifice, the gas flow downstream of the orifice will change accordingly. As such, if the regulator output drops by 10% as the cylinder is emptied, the resulting output flow from the orifice will drop by 10% and the diluted gas concentration will also drop by 10%, assuming the dilution flow rate is constant. If this is acceptable in the application, no further compensation is required. Optionally, to enhance the system accuracy, the cylinder pressure can be monitored by transducer 21 and in turn the dilution flow rate may be automatically adjusted to maintain a constant resulting gas concentration. It is also possible to omit transducer 21, and instead to use the controller 27 to read the cylinder pressure, recompute the actual output concentration as the cylinder drains, and communicate the resulting output concentration to some external device or simply report the resulting concentration on a display.

The apparatus shown in FIG. 1 supplies a single gas to an apparatus to be tested, it may supply multiple gases if the miniature cylinder contains two or more concentrated gases. Apparatus may also be constructed to supply multiple gases, either individually or in combination. These are the embodiments shown in FIGS. 2 and 3.

Figure 2:
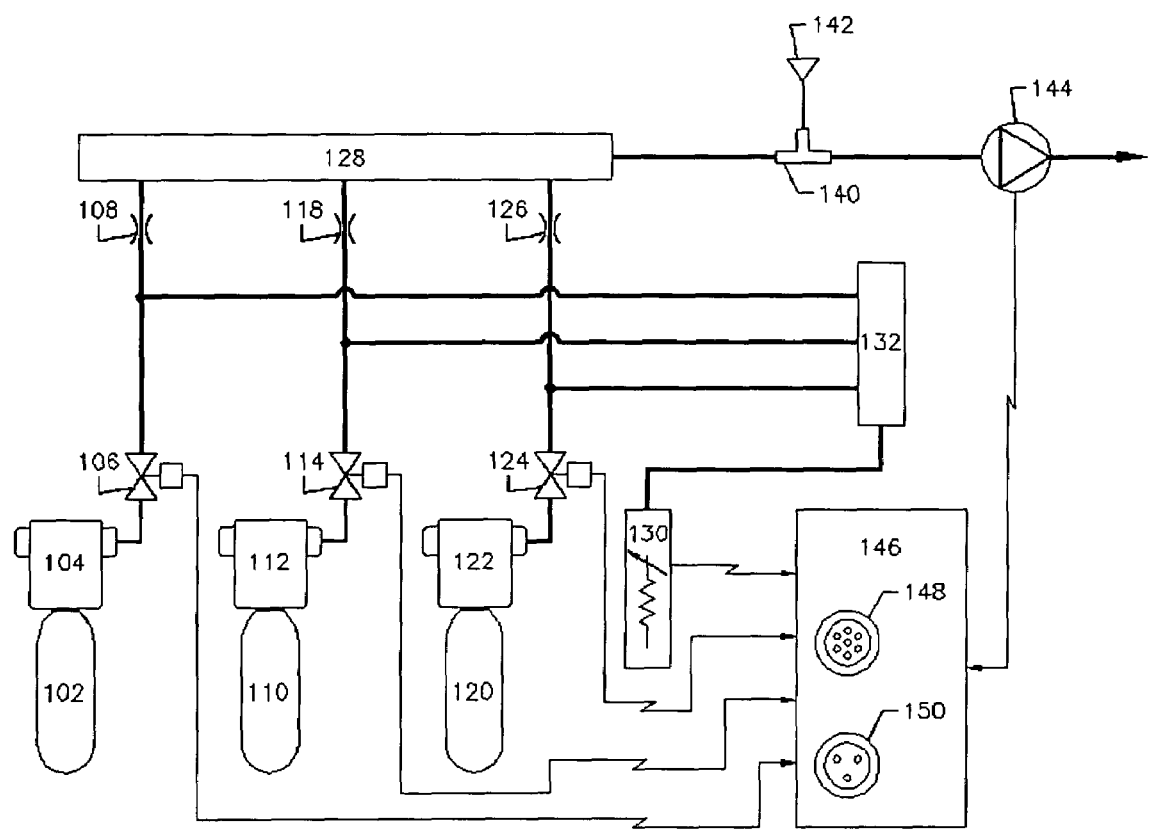
FIG. 2 is a schematic representation of a multiple gas generator according to a further embodiment of the invention.

FIG. 2 shows schmatically an apparatus with three miniature cylinders 102, 110 and 120 connected respectively to receptacle/regulators 104, 112 and 122, solenoid valves 106, 114 and 124 and micro orifices 108, 118 and 126. Each gas line from the micro orifices opens into a common manifold 128 from which gas is pumped by pump 144. Dilution of the gas is accomplished by the provision of a tee 140 which admits air through an air filter 142.

Pressure in the system is measured by a single pressure transducer 130 connected to a single pressure switch 132 which is connected to each gas circuit. A control system 146 operates the apparatus, with data port 148, and connector 150 supplying power to the system.

Figure 3:
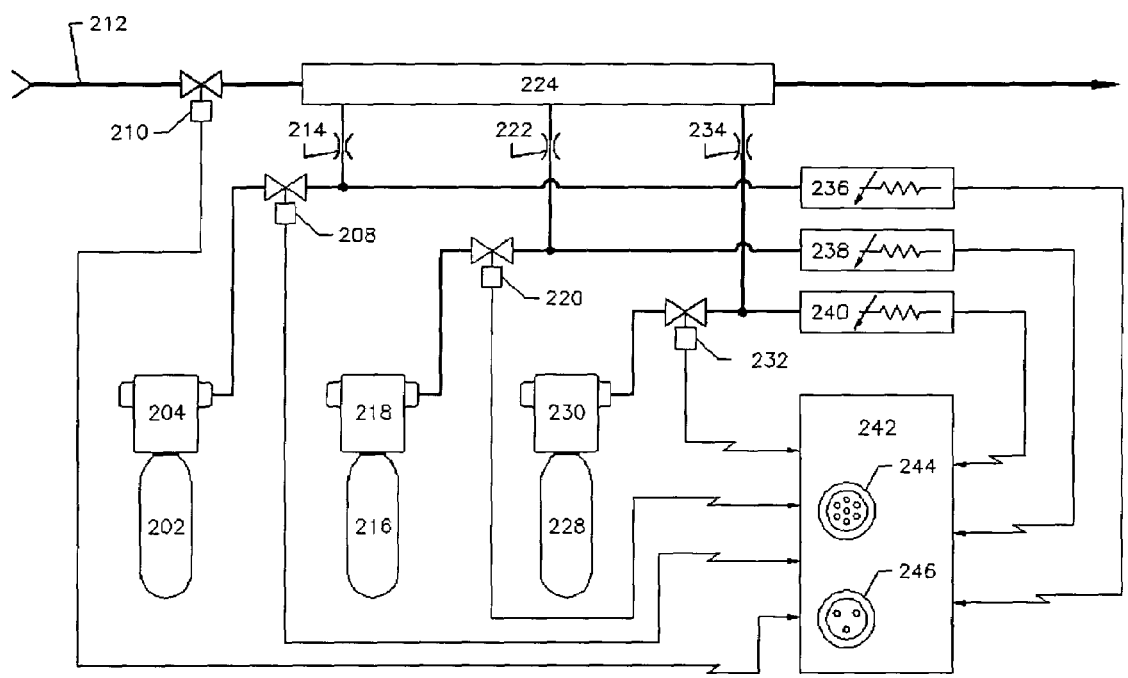
FIG. 3 is a schematic representation of a multiple gas generator according to another embodiment of the invention.

In a further embodiment shown in FIG. 3, there are three miniature cylinders 202, 216 and 228, connected respectively to receptacles/regulators 204, 218 and 230, solenoid valves 208, 220 and 232 and micro orifices 214, 222 and 234. Each gas line from the micro orifices opens into a common manifold 224. Instead of a pump and tee to dilute the air, air is provided by a compressed gas source 212, which releases air into the manifold 224 when solenoid valve 210 is activated.

Each gas line from a miniature cylinder is equipped with its own pressure transducer 236, 238 and 240, respectively. Operation of the apparatus is controlled by a control system 242 with a data port 244 and a power connector 246.

Various differences can be seen in the embodiments of the figures representing differing manners in which the functions of the apparatus can be performed.

For example, in FIG. 1, the pressure transducer 21 is connected to the manifold, and employed to monitor the pressure at the outlet of the receptacle 11. Alternately, this pressure regulator could also directly monitor the cylinder pressure upstream of the manifold as shown in FIG. 2 and FIG. 3. Data output from the pressure transducer is fed into the control unit in each embodiment, and then used to compensate for flow rate changes. Alternately, the pressure transducer can be used to simply indicate when the pressure in the circuit is below a predetermined level, and in this case, a valve would be closed or opened, notifying the control unit that the cylinder is below the recommended operating level and should no longer be used.

The apparatus includes an air dilution system. This dilution system may include either a compressed air line or a small self-contained pump 31 in FIG. 1 and 144 in FIG. 2. For ultimate portability, the preferred air dilution system is a small air sampling pump 31. When used as a gas generation station or in a fixed point application, the pump can be replaced by a compressed air line 212 in FIG. 3. In many industrial facilities, an air compressor is required for various types of equipment that need clean, dry air to operate. Use of this available compressed air will save on both the initial cost of the apparatus and projected maintenance costs in the future.

Together with the air dilution source, a gas mixing "tee" fitting 33 in FIG. 1, and 140 in FIG. 2, is used. In FIG. 3, a specific tee fitting is eliminated, with part of manifold 224 serving this purpose, to mix the dilution air with the pure or concentrated compressed gas. When a tee fitting is used, air as a diluting gas is drawn into the tee at a fixed flow rate by motorized air pump 31 and 144. The flow rate of the pump is predetermined and pre-set, typically by adjusting the voltage supplied to the pump. The flow rate of the compressed air source 212 can also be determined and preset via a pressure regulator.

The pumps 31 and 144 draw air from the surrounding atmosphere at a constant, steady flow rate, and air filters 29 in FIG. 1 and 142 in FIG. 2 are used to condition the air for use. The filter may contain porous materials that filter out dust and particulates, and activated charcoal that can remove molecules such as VOC's, and $H_2S$, $SO_2$, etc. Other chemical filters can be used for particular gases. The compressed air source 212 may also include some type of filtering (not shown) as necessary and may also include a separate solenoid 210 for switching on and off the compressed air to be provided to the apparatus. The resulting gas stream mixture containing the gas and air is then supplied to a calibration system connected to the generator through appropriate tubing.

Many variables affect the flow through orifices. One variable is the orifice diameter; flow varies directly with the area of the hole or is a function of the square of the diameter.

Other variables include the pressure of gas across the orifice, the shape of the entrance, and the depth of the orifice relative to its diameter. However, the flow rate of any gas can be predicted, regardless of conditions, if the orifice has been flow calibrated under a controlled and known set of conditions. Standard orifices used in flow calibration have been compared to N.I.S.T. flow calibrated orifices and found to be accurate to ±0.5%. Accurate gas mixtures can then be made using calibrated orifices.

The micro orifices used according to the invention are precision orifices typically having a diameter of 0.5 to 50 µm.

The following formula has been used by Lenox Laser, Inc., Glen Arm, Md., USA to determine a required orifice diameter and to calculate flows of other gases under other conditions after an orifice has been flow calibrated.

$$\text{Flow} = 0.01749 \times \frac{p_1 D^2}{29.7} \times \sqrt{\frac{15312}{M \times t}} \times \left(\frac{\Delta p}{p_1} \text{factor}\right)$$

where

Flow=flow rate in cubic centimeters/minute;
$p_1$=inlet pressure in psi absolute;
$\Delta P$=difference in inlet pressure and outlet pressure in psi;
D=orifice diameter in micrometers;
$\Delta p/p_1$ factor=a factor used to calculate gas flow when $\Delta p/p_1$ is less than 0.5;
M=molecular weight of gas or gas mixture; and
t=temperature in degrees Celsius.

In the formula shown, proportional factors are used to determine flow rates for different basic changes such as inlet pressure, outlet pressure, temperature, molecular weight of gases, etc. The flow of air or gas under standard conditions is equal to $0.1749 \times D^2$. $\Delta p/p_1$ factor applies only when $\Delta p/p_1$ is <0.5; otherwise this factor is 1. When $\Delta p/p_1$ is more than 0.5, gas velocity through an orifice is at the speed of sound and the standard flow rate is directly proportional to the absolute pressure. When $\Delta p/p_1$ is less than 0.5, the flow curve is empirical and cannot be satisfied with an equation so a correction factor must apply. The actual values of the factor are obtained through experimentation. Since air is used as the standard gas to calibrate the flow and select the orifice sizes, the flow of other gases is proportional to air by the ratio $(M_{air}/M_{gas})^{1/2}$ if all other conditions are held constant.

According to this equation, the diameter of the micro orifice needed for a specific gas can be calculated. For example, when the inlet and outlet pressures are 17 psig and 1 atmosphere, respectively, the diameter should be 1.6 µm for carbon monoxide gas to flow at a rate of 0.05 ml/min. When this gas is blended with air at a flow rate of 500 ml/min, a 100 ppm by volume CO concentration is obtained. The diameters of orifices for other gases and concentrations can be calculated in the same way.

The gas flow coming from the pure or concentrated gas source is negligible compared to the gas flow from the air source. For example, in order to generate 100 ppm CO at 500 ml/min, the flow rate of CO should be 0.05 ml/min if it's pure, and 0.5 ml/min if the CO concentration is 10% in the cylinder. These gas flow rates are negligible when compared to 500 ml/min so the total flow will not significantly change after adding the gas portion of flow to the air stream. This should greatly simplify the design and costs of the apparatus as a fixed flow air pump can be utilized. It also makes it simple to add other gases to the gas delivery line.

The invention enables a gas generator to be built in the same fashion as a modern inkjet printer with multiple compressed gas cylinders for generating more than one gas at a time. This is the embodiment shown in FIG. 2, which is a generator with three gas sources, each gas source being a disposable miniature cylinder filled with a concentrated gas 102, 110 and 120, respectively. The flow rate of each gas is individually controlled through pressure regulators 104, 112, 122 and micro orifices 108, 118, 126. Air as a diluting gas is delivered at a fixed flow rate using motorized air pump 144. In the example of FIG. 2, only one pressure transducer 130 is needed to measure the pressure of all three cylinders by combining the pneumatic circuits through pressure switch 132. To accomplish this, cylinder pressures can be measured discretely as solenoids 106, 114 and 124 are independently switched on during use, or as part of a start-up diagnostic self-test. Use of this configuration will likely save costs by use of a single solenoid for any number of cylinder combinations as opposed to the use of one solenoid per gas cylinder as in FIG. 3. An important operational requirement of this method is to allow the line pressure to bleed off between sequential solenoid activations; otherwise, the residual gas in the line may diffuse back into the other cylinders inadvertently, thereby causing contamination of the gases. Bleed off can be accomplished either by waiting for a fixed amount of time between each solenoid access, or by actively monitoring the actual pressure transducer signal until the reading drops below an acceptable level before the next solenoid access.

FIG. 3 differs from the embodiment of FIG. 2 in that it is configured using a pressure switch/transducer 236, 238 and 240 respectively for each of cylinders 202, 216 and 228. Use of this configuration alleviates the need to bleed off excess pressure between successive solenoid activations and also allows the control unit 242 to continuously monitor each cylinder pressure independently during use. No start-up diagnostics and sequential switching of cylinders is required to determine cylinder pressure. FIG. 3 also differs from the embodiments shown in FIGS. 1 and 2 in its use of a compressed gas source 212 placed upstream of manifold 224 as the source of dilution gas. Manifold 224 also serves as the gas dilution tee. It is also to be noted that manifold 128 in FIG. 2 could act as a gas dilution tee if properly configured, and that pumps 31 and 144 in FIGS. 1 and 2 could be configured to pressurize manifolds 19 and 128 as opposed to drawing a vacuum as shown.

A compact, automated test station can be built with this generator for conducting testing and calibration on a regular basis with multiple instruments with different single and multiple sensor configurations. The generator can be instructed by computer software to produce either a single gas, or a mixture of several gases of appropriate concentrations for calibrating, or bump testing one or more instruments placed in a centralized docking station (calibration station). Control and feedback to and from the computer may be provided through data ports 39 in FIG. 1, 140 and FIG. 2 and 244 in FIG. 3 or via wireless communications, directly from the control unit. If the pressure, detected by the pressure transducer or switch, is below a certain level, a low gas message will be displayed by the computer, or the computer could use the measured cylinder pressure along with the pump or compressed air flow set-points to calculate the actual concentration of gas supplied by the apparatus. This data could then also become a feedback signal for use with the controlling computer or automated calibration docking station to accurately indicate what the true concentration is as the pressure changes.

It will be recognized that a variety of control schemes may be employed to reliably carry out the gas generation operation in the practice of the invention in any appropriate manner. Furthermore, although the foregoing description has been directed to a regulator and micro orifice as the upstream means of gas flow control, it will be recognized that a wide variety of other means could be employed, such as opening the solenoid valve to briefly release the gas to be blended into either flowing or stagnant air.

Thus, while the invention has been shown and described with reference to specific features, aspects and embodiments herein, it will be appreciated that the invention is relevant to a wide variety of other embodiments, features and implementations consistent with the disclosure herein, and the invention is therefore to be broadly construed and interpreted, within the spirit and scope of the foregoing disclosure.

What is claimed is:

1. An apparatus for providing calibration gas to a gas monitoring instrument, comprising:
    a calibration gas source comprising a miniature gas cylinder containing a calibration gas, and including a pierceable seal or open/close valve;
    an outlet for providing test gas to the monitoring instrument; and
    a gas conduit for providing diluted cylinder gas to the outlet, the gas conduit comprising:
    a receptacle means for receiving the miniature gas cylinder in gas-tight manner, and including means for rupturing the seal or opening the valve;
    a manifold;
    pressure transducer means for determining pressure of the gas in the conduit;
    a valve for releasing the gas into the gas conduit;
    a micro orifice for providing a controlled flow of calibration gas in the conduit;
    means for diluting gas in the conduit with air; and
    control means for releasing test gas to the conduit upon determination of sufficient pressure in the manifold.

2. The apparatus of claim 1, wherein the gas dilution means comprises a tee fitting with a leg of the tee fitting connected to a source of air.

3. The apparatus of claim 2, wherein the source of air is atmospheric air, and a filter is disposed between the atmospheric air and the tee fitting.

4. The apparatus of claim 3, additionally comprising a pump in combination with the tee fitting to provide a controlled flow of diluted calibration gas to the outlet.

5. The apparatus of claim 1, wherein the means for diluting comprises a source of compressed air connected by a valve to the conduit.

6. The apparatus of claim 1, wherein the gas source comprises a plurality of miniature gas cylinders, each cylinder being received in a said receptacle means.

7. The apparatus of claim 6, wherein each gas cylinder is connected to a common manifold, with a valve disposed between each receptacle means and the common manifold.

8. The apparatus of claim 7, wherein a single pressure transducer is connected between the valves and the common manifold.

9. The apparatus of claim 8, wherein the transducer controls a single pressure switch controlling flow of gas to the manifold.

10. The apparatus of claim 7, wherein a pressure transducer is connected between each valve and the common manifold.

11. The apparatus of claim 1, wherein the miniature gas cylinder has a volume of about 10–100 ml.

12. The apparatus of claim 1, wherein the receptacle includes a regulator.

13. The apparatus of claim 1, wherein the receptacle includes venting means for excess gas pressure.

14. The apparatus of claim 1, wherein the gas source is a single cylinder containing a plurality of gases.

15. The apparatus of claim 1, wherein the micro orifice has a diameter between 0.5 and 50 $\mu$m.

16. The apparatus of claim 1, wherein the calibration gas in the cylinder has a concentration of at least 0.1% by volume, and is diluted with a gas or gas mixture with which the calibration gas does not react.

17. The apparatus of claim 1, wherein the calibration gas in the cylinder has a concentration of 1–100% by volume.

18. The apparatus of claim 17, wherein the concentration is at least 98% by volume.

19. A method for providing a calibration gas to a gas detection instrument, comprising the steps of:
    disposing in a receptacle a miniature gas cylinder containing a calibration gas, and opening a seal in the cylinder to permit gas to flow into a gas conduit;
    determining pressure of the gas in the conduit, and verifying that said pressure is at least a predetermined level;
    passing the gas which is at least at said predetermined pressure through a micro orifice to control the flow of the gas to a predetermined rate;
    diluting the gas flowing at said predetermined rate with a diluting gas flowing at a known rate; and
    passing the diluted gas to an instrument to be calibrated.

20. The method of claim 19, wherein the calibration gas in the miniature cylinder has a concentration of at least 0.1% by volume, and is diluted with a gas or gas mixture with which the calibration gas does not react.

21. The method of claim 19, wherein the calibration gas in the cylinder has a concentration of 1–100% by volume.

22. The method of claim 21, wherein the concentration is at least 98% by volume.

23. The method of claim 19, wherein the orifice has a diameter between 0.5 and 50 $\mu$m.

24. The method of claim 19, wherein the diluting gas is filtered ambient air.

* * * * *